(12) United States Patent
Corwin et al.

(10) Patent No.: US 9,817,221 B2
(45) Date of Patent: Nov. 14, 2017

(54) SYSTEMS AND METHODS FOR PROCESSING AND IMAGING OF BIOLOGICAL SAMPLES

(71) Applicant: General Electric Company, Schenectacy, NY (US)

(72) Inventors: Alex David Corwin, Niskayuna, NY (US); Robert John Filkins, Niskayuna, NY (US); Jun Xie, Niskayuna, NY (US); Nannan Chen, Clifton Park, NY (US); Kashan Ali Shaikh, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 117 days.

(21) Appl. No.: 14/410,890

(22) PCT Filed: Jun. 26, 2013

(86) PCT No.: PCT/US2013/047814
§ 371 (c)(1),
(2) Date: Dec. 23, 2014

(87) PCT Pub. No.: WO2014/004622
PCT Pub. Date: Jan. 3, 2014

(65) Prior Publication Data
US 2015/0185453 A1    Jul. 2, 2015

Related U.S. Application Data

(63) Continuation-in-part of application No. 13/538,898, filed on Jun. 29, 2012, now Pat. No. 9,164,015.

(51) Int. Cl.
G02B 21/00    (2006.01)
G01N 1/31     (2006.01)
(Continued)

(52) U.S. Cl.
CPC .......... *G02B 21/008* (2013.01); *G01N 1/312* (2013.01); *G01N 35/00029* (2013.01);
(Continued)

(58) Field of Classification Search
CPC .. C12Q 1/02; C12Q 1/06; C12M 1/34; C12M 1/00; G01N 35/02; G01N 35/00; G06K 9/00
(Continued)

(56) References Cited

U.S. PATENT DOCUMENTS 5,355,439 A *  10/1994  Bernstein ............... B25J 9/1671
                                                   700/247
7,318,913 B2 *  1/2008  Loeffler .................. B01L 3/502
                                                    251/337
(Continued)

FOREIGN PATENT DOCUMENTS

WO          0142796 A1      6/2001

OTHER PUBLICATIONS

International Search Report and Written Opinion dated Nov. 21, 2013 which was issued in connection with PCT Patent Application No. US2013/047814 which was filed on Jun. 26, 2013.

*Primary Examiner* — Seung C Sohn
(74) *Attorney, Agent, or Firm* — Eversheds Sutherland (US) LLP (57) ABSTRACT

A method for processing and imaging a first and second plurality of samples, comprising processing at least one sample from the first plurality of samples, imaging the at least one sample from the first plurality of samples, while being capable of simultaneously processing at least one sample from the second plurality of samples; and imaging the at least one processed sample from the second plurality of samples.

16 Claims, 7 Drawing Sheets

(51) Int. Cl.
*G01N 35/00* (2006.01)
*G01N 1/30* (2006.01)

(52) U.S. Cl.
CPC .......... *G01N 35/0092* (2013.01); *G01N 1/30* (2013.01); *G01N 35/0099* (2013.01)

(58) Field of Classification Search
USPC .................. 250/576; 435/29, 39; 436/44, 48
See application file for complete search history.

(56) References Cited

U.S. PATENT DOCUMENTS

| | | | |
|---|---|---|---|
| 7,744,817 B2 * | 6/2010 | Bui ........................ | G01N 1/312 422/561 |
| 8,673,643 B2 * | 3/2014 | Corwin .................. | G01N 1/312 427/2.13 |
| 9,164,015 B2 * | 10/2015 | Corwin .................. | G01N 1/312 |
| 2006/0088928 A1 | 4/2006 | Sweet et al. | |
| 2008/0113440 A1 | 5/2008 | Gurney et al. | |
| 2009/0269799 A1 | 10/2009 | Winkelman et al. | |
| 2010/0183216 A1 | 7/2010 | Yamada | |
| 2011/0014645 A1 | 1/2011 | Winkelman et al. | |
| 2011/0070606 A1 | 3/2011 | Winkelman et al. | |
| 2012/0135458 A1 | 5/2012 | Corwin et al. | |
| 2012/0149050 A1 | 6/2012 | Lapen et al. | |

* cited by examiner

SYSTEMS AND METHODS FOR PROCESSING AND IMAGING OF BIOLOGICAL SAMPLES

BACKGROUND

The invention relates to molecular pathology, and more particularly to systems and methods for processing and imaging biological samples.

Biological samples are used for analytic and diagnostic purposes, such as diagnosing diseased tissue at a molecular level. A biological sample, such as tissue sections or tissue micro arrays (TMA) typically stained with a morphological stain or biomarker are analyzed manually with a microscope. Alternatively, an image of the tissue is acquired for subsequent analysis or comparison. After the first stain is applied and imaged, one or more serial or successive stains or biomarkers may be applied and the tissue may be analyzed again. The two or more serial images may then be compared. A single staining cycle may comprise the steps of applying a stain (antibody) over the tissue, incubating the stain for an appropriate time, rinsing away the stain to reduce background fluorescence, imaging the slide, and bleaching away the stain. In multiplexed applications, where one or more samples are stained with a plurality of stains, sequential staining, rinsing, and bleaching cycles may be required. For example in multiplexed applications, the tissue may need to be stained with multiple molecular probes to investigate protein expression or spatial distribution quantitatively or qualitatively. Thus, the total time of operation is generally a sum of time required for each of these steps multiplied by the total number of applied stains.

The staining process is typically performed using time-consuming manual techniques that are susceptible to error. Further, the image acquisition unit, such as a microscope, is usually idle during the time when the samples are being processed for imaging. Similarly, when the samples are being imaged, sample processing devices such as staining devices, may remain idle. In instances where the image acquisition unit or sample processing unit is left idle during the time when the sample is with the other unit, the overall time of the process may increase significantly.

Therefore, it is desirable to provide systems and methods for processing and imaging the biological samples with enhanced throughput and reduced idle time. It is also desirable to provide an automated process that reduces manual intervention and overall cost associated with the idle time of components of the system.

BRIEF DESCRIPTION

A method for processing and imaging a first and second plurality of samples, comprising processing at least one sample from the first plurality of samples, imaging the at least one sample from the first plurality of samples, while also being capable of simultaneously processing at least one sample from the second plurality of samples; and imaging the at least one processed sample from the second plurality of samples.

An automated method for processing and imaging a plurality of samples, comprising processing at least one sample while imaging another one or more samples, wherein processing comprises staining, rinsing, bleaching, applying an imaging solution, optionally applying a coverslip, optionally removing a coverslip, or combinations thereof.

In one embodiment, a system for processing and imaging a plurality of samples comprises a sample processing unit configured to process one or more of the plurality of samples, an image acquisition unit operatively coupled to the sample processing unit; and a sample conveyance unit configured to transport one or more of the plurality of samples to the sample processing unit, image acquisition unit, or both, wherein the system is configured to process at least one sample from the plurality of samples while imaging another sample from the plurality of samples.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Embodiments relate to molecular pathology systems and methods for processing and imaging biological samples. The systems and methods may reduce or eliminate idle time otherwise associated with a sample processing unit, an image acquisition unit, or both. In certain embodiments, the systems and methods for processing and imaging the biological samples may be automated. In these embodiments, the systems and methods may operate with minimal operator intervention, e.g., by reducing or eliminating the need to transfer samples (e.g., tissue samples within a flow cell).

To more clearly and concisely describe the subject matter of the claimed invention, the following definitions are provided for specific terms, which are used in the following description and the appended claims. Throughout the specification, exemplification of specific terms should be considered as non-limiting examples.

As used herein, the term "biological sample" refers to a sample obtained from a biological subject, including sample of biological tissue or fluid origin obtained in vivo or in vitro. Such samples may be, but are not limited to, tissues, fractions, fluids and cells isolated from mammals including, humans. In some embodiments, the biological sample includes tissue sections of colon, normal breast tissue, prostate cancer, colon adenocarcinoma, breast tissue microarray, breast TMA, or normal prostrate. A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to two or more different targets (at morphological or molecular level). In some embodiments, the same section of tissue sample may be analyzed at both morphological and molecular levels. A tissue section, if employed as a biological sample, but is not limited to, may have a thickness in a range that is less than about 100 microns, in a range that is less than about 50 microns, in a range that is less than about 25 microns, or in range that is less than about 10 microns.

As used herein, the term "probe" refers to an agent comprising a binder, a signal generator or both. In some embodiments, the binder and the signal generator of the probe are embodied in a single entity (e.g., a radioactive or fluorescent molecule capable of binding a target). In alternative embodiments, the binder and the signal generator are embodied in discrete entities (e.g., a primary antibody capable of binding target and labeled secondary antibody capable of binding the primary antibody).

As used herein, the term "binder" refers to a biological molecule that may non-covalently bind to one or more targets in the biological sample. A binder may specifically bind to a target. Suitable binders may comprise one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, electrical signal, or radioactive signal. In one example, the signal generator may comprise a lumiphore, a fluorophore, or both.

As used herein the term "lumiphore" refers to a chemical compound that demonstrates luminescence including chemoluminescence, bioluminescence, phosphorescence, and photoluminescence. Representative examples include, but are not limited to, luminol, lucigenin, acridans, acridinium esters, and dioxetanes, and fluorophores.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), fluorescamine derivative (fluorescent upon reaction with amines); IR144; IR1446; malachite green isothiocyanate; 4-methylumbelliferone; ortho cresolphthalein; nitrotyrosine; pararosaniline; phenol Red, B-phycoerythrin; o-phthaldialdehyde derivative (fluorescent upon reaction with amines); pyrene and derivatives such as pyrene, pyrene butyrate and succinimidyl 1-pyrene butyrate; reactive red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine, tetramethyl rhodamine isothiocyanate (TRITC); riboflavin; rosolic acid and lathanide chelate derivatives, quantum dots, cyanines, and squaraines.

As used herein the term 'oxidant" or "oxidizing agent" refers to a bleaching reagent that substantially inactivates a signal generator. Representative oxidizing agents comprise active oxygen species, hydroxyl radicals, singlet oxygen, hydrogen peroxide, or ozone such as hydrogen peroxide, potassium permanganate, sodium dichromate, aqueous bromine, iodine-potassium iodide, and t-butyl hydroperoxide.

In certain embodiments, the method for processing and imaging comprises providing a first plurality of samples and a second plurality of samples, processing at least one sample from the first plurality of samples, imaging the processed samples from the first plurality of samples, while simultaneously processing at least one sample from the second plurality of samples, and then imaging the processed samples from the second plurality of samples while optionally further processing samples from the first plurality of samples. In some embodiments, the plurality of samples may comprise one or more groups of samples. In embodiments where the plurality of samples comprises two or more groups of samples, the groups of samples may be disposed at a distance from each other. The distance between the groups may be such that samples of at least one group may be subjected to processing, while the samples of another one or more group are being imaged, or vice versa. In one embodiment, the samples in a group may be disposed in an array or any irregular pattern.

In certain embodiments, a system for processing and imaging a plurality of samples may comprise a sample processing unit, an image acquisition unit, and a sample conveyance unit. In one embodiment, the system may comprise two or more image acquisition units. The sample processing unit may be configured to process one or more of the plurality of samples before or after imaging. In one embodiment, the image acquisition unit may be operatively coupled to the sample processing unit such that the processed samples may be imaged using the image acquisition unit. In one embodiment, the sample conveyance unit may be configured to transport one or more of the plurality of samples to the sample processing unit, image acquisition unit, or both. In one example, the sample conveyance unit may be configured to transport the samples between the sample processing unit and the image acquisition unit. In another example, the sample conveyance unit may be configured to transport the samples from a different location to the sample processing unit, image acquisition unit, or both. For example, the sample conveyance unit may be configured to transport the samples from a sample repository to the sample processing unit, and from the sample processing unit to the image acquisition unit. In some embodiments, the system may be configured to process at least one sample from the plurality of samples while imaging another sample from the plurality of samples. In one embodiment, the sample conveyance unit may be in the form of a conveyor belt, a robotic arm, a movable sample stage, or combinations thereof.

In some embodiments, the sample processing may comprise a plurality of steps, where each step comprises an associated processing time. Non-limiting examples of the sample processing steps may comprise staining, rinsing, bleaching, applying an imaging solution, optionally applying a coverslip, optionally removing a coverslip, or combinations thereof. One or more of the plurality of steps for the sample processing may also comprise an associated incubation period. In one example, the step of applying a staining reagent may have an associated incubation period. In another example, the sample may be incubated for a determined period of time after applying the staining reagent to provide sufficient time for the antibodies to bind with the molecules in the biological sample. The incubation periods associated with one or more sample processing steps may further increase the total time required for the sample processing.

As will be appreciated, sample processing and imaging are distinct operational steps that are not performed simultaneously in a system. In one example, imaging may be performed after processing the samples. In another example, the imaging may be performed both before and after processing the samples.

In certain embodiments, the systems and methods may increase the throughput of the molecular pathology system by planning sample processing and imaging steps such that individual idle times associated with the sample processing unit, image acquisition unit, or both are reduced. Reducing the idle time of the sample processing unit, image acquisition unit, or both may also reduce the cost associated with the operation of the system. In one embodiment, the individual idle times for the sample processing unit and image acquisition unit may be minimized. In one example, an idle time associated with the image acquisition unit between imaging a first sample and a last sample of a plurality of samples may be about 0 mins. In this example, the samples may be sequentially imaged one after another with no measurable time difference between two consecutive samples. Hence, scheduling or planning the sample processing and imaging steps such that a sample processing unit and an image acquisition unit are maintained in idle position for minimal amount of time, may increase the throughput of the system.

In certain embodiments, the throughput of the system may be increased by optimum grouping of samples, such as grouping the sample to achieve minimum time-to-completion. For example, a low magnification image of each sample may be acquired to determine the scan area of each sample, and the samples may then be grouped into the first and second plurality of samples based on the scan area of each sample. Using the scan area, scan time may be predicted for each sample, and the first and second plurality of samples may be groups such that about the same scan time is needed for each group, i.e., achieving equal batch sizes based on scan area.

In another example, the sample is grouped into first and second plurality of samples based on the scan area of each sample, as well as information about the assays, when the samples are subjected to a mix of different assays. This combined information is used to predict throughput for the batch, and samples are grouped accordingly. The information about the assays may include: what assay is to be performed, how many rounds it will take, as well as the total scanning area.

$$\text{Total time} = \Sigma[(\text{scanRate} * \text{tissue\_area}) + \text{number of dye\_colors} + \text{number rounds}]$$

In certain embodiments, the systems and methods may increase the throughput of the molecular pathology system by imaging the first and second plurality of samples before any processing is performed to obtain background images.

In certain embodiments, the systems and methods may increase the throughput of the molecular pathology system by imaging one of the first or the second plurality of samples, prior to processing, to establish background images, while the other set of sample is being processed.

In some embodiments, a plurality of samples may be processed simultaneously or sequentially. The plurality of samples may also be imaged in a sequential or simultaneous manner.

In certain embodiments, simultaneously processing the plurality of samples may comprise performing at least one of the processing steps concurrently for one or more samples. Simultaneously processing the plurality of samples may enable maximizing the utilization of the sample processing unit and image acquisition unit, and reducing the total time of operation. In one example, one or more samples may be stained simultaneously, the stain used for the one or more samples may be same or different. The incubation period associated with the step of staining may be the same or different for the one or more samples.

In some embodiments, the plurality of samples may be divided into two or more groups. In these embodiments, the process may commence with the staining of one or more samples of a first group. Some or all of the samples of a group may be processed simultaneously. After processing, the samples of the first group may be imaged. While imaging the processed samples of the first group, samples from the second group of samples may be processed. Hence, if the processing time of a sample of the second group is less than or equal to the cumulative imaging time of the processed samples of the first group, the samples of the second group may be made available for imaging immediately after the samples of the first group are imaged. Hence, both the sample processing unit and image acquisition unit may be kept idle for minimal duration between processing of the first sample and imaging of the last sample of the plurality of samples.

In certain embodiments, multiplexing or multiplexed analysis may generally refer to analysis of multiple targets in a biological sample using the same detection mechanism. In molecular imaging, a signal generator (e.g., fluorophore) may be excited and the signal (e.g., fluorescence signal) obtained may be observed and recorded in the form of a digital signal (for example, a digitalized image). For multiplexing, a similar procedure may be repeated for the plurality of different signal generators (if present) that are bound in the sample using the appropriate fluorescence filters. In some embodiments, a series of probes may be contacted with the biological sample in a sequential manner to obtain a multiplexed analysis of the biological sample. In some embodiments, a series of probe sets (including at most four probes in one set) may be contacted with the biological sample in a sequential manner to obtain a multiplexed analysis of the biological sample.

In one example where two groups of samples are used in a multiplexed application, the samples of a first group may be transported to the sample processing unit for processing (e.g., staining with a first stain). The samples of the first group may then be transported to the image acquisition unit for imaging. Subsequent to imaging, the samples of the first group may be transported to the processing unit for staining with a second stain, and then transported back to the image acquisition unit for imaging. Accordingly, the samples may be transported between the sample processing unit and the image acquisition unit multiple times depending on the number of stains used in the multiplexing application. Similarly, the second group of samples may be transported back and forth between the sample processing and image acquisition units depending on the number of stains.

In some embodiments, the plurality of samples may be received by a sample conveyance unit. The sample conveyance unit may comprise a movable portion that is configured to transport the samples between the sample processing unit and image acquisition unit. In one embodiment, the sample conveyance unit may be configured to transport the samples between the sample processing unit and image acquisition unit one or more number of times. In one example, the sample conveyance unit may be able to transport the samples back and forth between the sample processing unit and image acquisition unit. For example, in the case of multiplexing applications the samples may be transported to the sample processing unit for a first stain. Next, the samples may be transported to the image acquisition unit for imaging. Subsequently, the samples may be transported to the sample processing unit for a second rounding of staining using a different stain. The samples may be transported back and forth multiple number of times between the sample processing unit and image acquisition unit depending on the number of stains used for multiplexing.

In one example, the samples may be physically divided into two or more groups, where each group comprises one or more samples. The groups may be disposed or positioned on the sample conveyance unit such that the samples of one group may be imaged while samples of the other group are being processed. The optimal number of samples disposed on the sample stage may be determined based on the ratio of the imaging time and the sample processing time for an individual sample.

Figure 1:
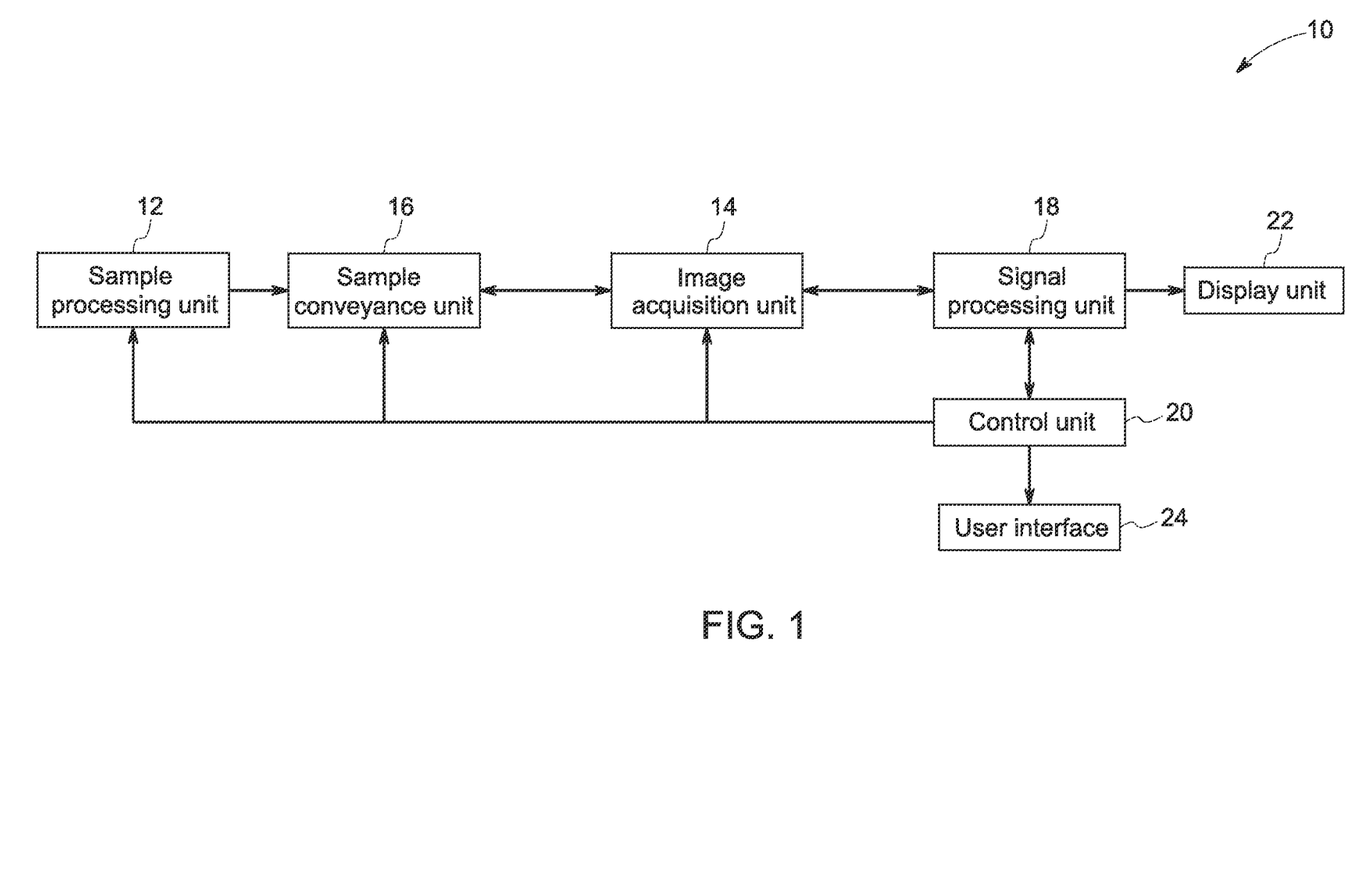
FIG. 1 is a block diagram of an example system for processing and imaging biological samples.

FIG. 1 illustrates an example of an integrated sample processing and imaging system 10. The system 10 may be an automated molecular pathology system. The system 10 may comprise a sample processing unit 12, an image acquisition unit 14 and a sample conveyance unit 16. The sample processing unit 12 may be configured to process the samples before or after imaging. In certain embodiments, the sample processing unit 12 may be configured to perform one or more processing steps such as, but not limited to, staining, rinsing, bleaching, or combinations thereof. In one embodiment, the sample conveyance unit 16 may be configured to receive a plurality of samples. The sample conveyance unit 16 may provide the samples to the sample processing unit 12. The image acquisition unit 14 may be configured to image the samples and provide imaging signals to a signal processing unit 18. The imaging signals may be processed and/or analyzed at the signal processing unit 18. The signal processing unit 18 may be operatively coupled to a display unit 22 to display the processed data.

In one embodiment, the sample conveyance unit 16 may be a part of the image acquisition unit 14 of the system 10. In one example, the sample conveyance unit 16 may be the stage of the image acquisition unit 14. For example, the sample conveyance unit 16 may be a stage of a microscope. In this example, the operations comprising sample processing and imaging may occur on the microscope stage. In another example, the sample conveyance unit 16 may be a separate entity from the image acquisition unit 14. In this example, the sample stage may be a motorized stage that may be operatively coupled to the image acquisition unit during operation.

In another embodiment, the sample conveyance unit 16 may be a separate entity from the image acquisition unit 14 that is configured to be operatively coupled to the image acquisition unit 14 and sample processing unit 12. In certain embodiments, the sample conveyance unit 16 may be configured to selectively transport the samples to the sample processing unit 12, image acquisition unit, or both. In one embodiment, the sample conveyance unit 16 may be configured to transport the samples to the sample processing unit 12, image acquisition unit, or both, from another location, such as but not limited to a sample repository. In another embodiment, the sample conveyance unit 16 may be configured to transport the samples back and forth between the sample processing unit 12 and image acquisition unit 14. In this embodiment, if the system 10 employs two or more image acquisition units, the sample conveyance unit 16 may be configured to transport the samples between the sample processing unit and the two or more image acquisition units. In one example, the sample conveyance unit 16 may be configured to transport the samples to the sample processing unit 12 for each of the staining, rinsing and bleaching steps. The sample conveyance unit 16 may be configured to transport the samples to the image acquisition unit 14 before or after the staining, rinsing or bleaching steps for imaging.

The sample conveyance unit 16 may be configured to undergo a translational movement, rotational movement, or both. In one embodiment, the rotational movement may comprise oscillatory movement. In certain embodiments, the sample conveyance unit 16 may comprise a conveyor belt, a robotic arm, a movable sample stage, or combinations thereof. The sample conveyance unit 16 may be configured to receive one or more groups of samples. The sample conveyance unit may be configured to dispose the one or more groups of the samples in discrete locations, such that when the samples from one group are being imaged at the image acquisition unit 14, samples from another group may be processed at the sample processing unit 12.

The movement of the sample conveyance unit 16 may be controlled using a control unit 20. The control unit 20 may be configured to control at least in part the sample processing unit 12, image acquisition unit 14, sample conveyance unit 16, or combinations thereof. In some embodiments, the control unit 20 may be in communication with a control input or user interface 24. In some embodiments, the sample conveyance unit 16 may comprise a driving device, such as a mechanical drive member, or an actuator to facilitate the sample conveyance unit 16 to move translationally, rotationally, or both. The driving device may be configured to receive inputs or commands from the control unit 20, user interface 24, or both.

In certain embodiments, the system 10 may be an automated system. The automated system 10 may require minimal operator intervention during imaging and processing of the plurality of samples. In one embodiment, automation may be achieved through computer control of one or more of the process steps involved in the sample processing, also referred to as, staining cycle, such as but not limited to, addition of staining reagents and oxidant. In certain embodiments, the image acquisition components (e.g., microscope or camera) may be controlled by software such as a program written in LabVIEW or C.

In some embodiments, the automation of the sample processing steps may be achieved by using a robotic device. Provisions may be provided to incorporate unforeseen alterations in planned processing steps. For example, provisions may be provided to alter staining time or incubation period for a step during the processing of the samples. Further, the system 10 may be configured to suggest operator actions. The suggested operator actions may be displayed. In one example, the system 10 may be configured to propose a schedule for sample processing for one or more samples depending on the incubation period etc. for the stain. In embodiments where there are two or more groups, the system 10 may propose the order of the groups for processing and imaging.

In certain embodiments, the automated system 10 may comprise acquiring or accepting or accessing information such as protocol or reagent information, transmitting such information to at least one sample processing system or even a stand alone processor, and processor systems. Furthermore, embodiments may provide: for handling, maintaining, sharing, and using the sample processing information. These aspects may be provided for individual samples or group of samples, as pre-fed data or in a real-time manner.

In some embodiments, the system 10 may provide for a real-time information display. In embodiments having real-time information display, the display unit 22 may display the information about the time it occurs. In one example, real time information display may be provided to a remote location, thereby enabling the operator or user to monitor the progress of the process from a remote location, such as home or another lab. In some embodiments, the automated system 10 may be controlled by hardware, software, or a combination thereof. In these embodiments, the sample processing and imaging steps for one or more groups of samples may be planned and executed using computer-aided means.

Figure 2:
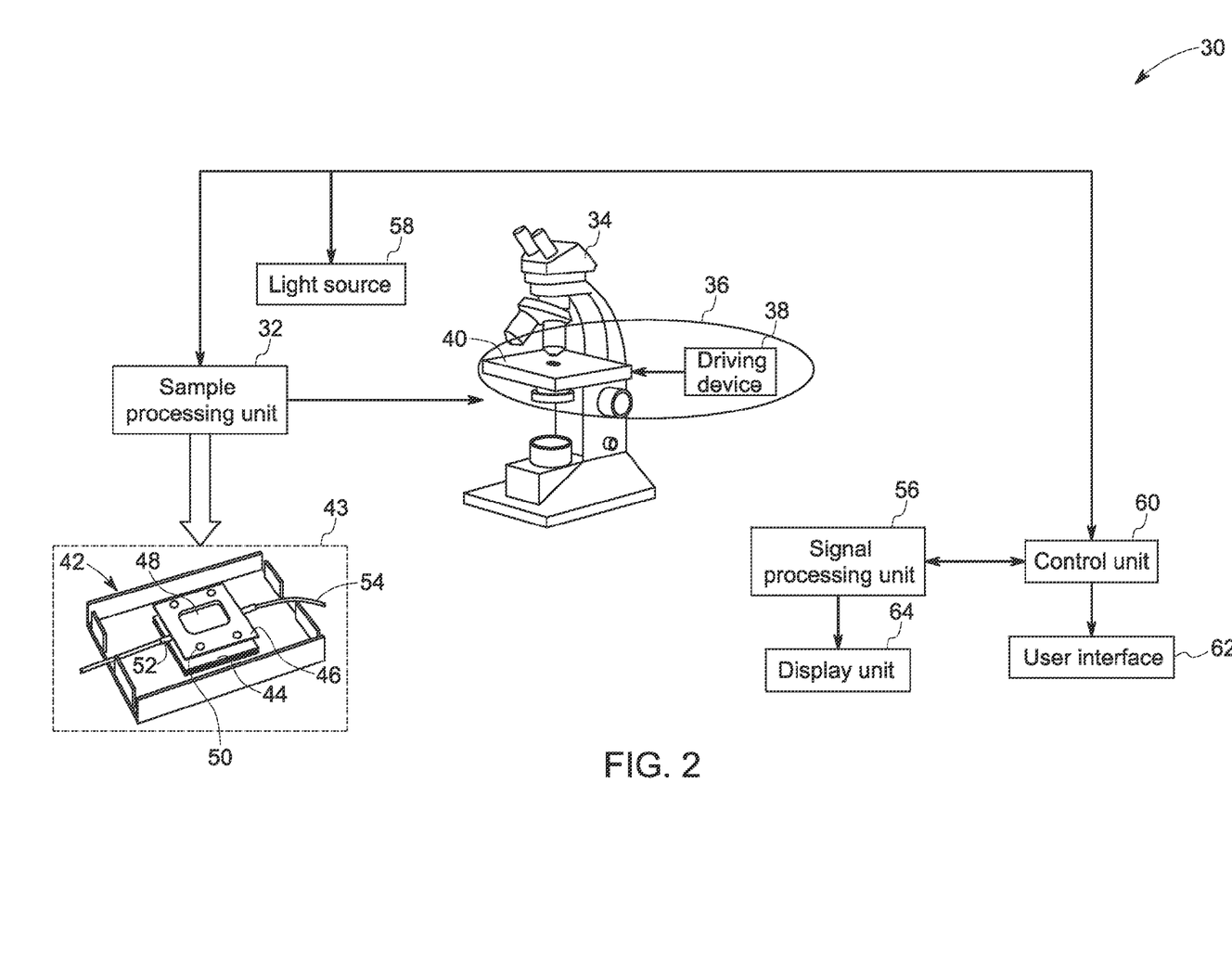
FIG. 2 is a block diagram of an example system for processing and imaging biological samples disposed in respective flow cells on a sample stage.

FIG. 2 illustrates a detailed diagram of an example integrated sample processing and imaging system 30. The system 30 may be an automated molecular pathology system. The system 30 may comprise a sample processing unit 32, image acquisition unit 34, and sample conveyance unit 36. The sample conveyance unit 36 may comprise a sample stage 40 and driving device 38. In the illustrated embodiment, the sample stage 40 is an integral part of the image acquisition unit 34.

The system 30 comprises flow cells 42. An enlarged view of the flow cells 42 is illustrated in the dashed rectangle 43. The flow cells 42 may comprise a solid support-receiving member 44, a gasket 46 with an opening configured to receive a sample disposed on a slide 48, a lid 50, an inlet port 52, and an outlet port 54. Each flow cell 42 defines a closed chamber where the slide 48 is positioned in the slide-receiving member 44. The gasket 46 may be disposed between the slide 48 and the lid 50. As the flow chamber is enclosed inside the flow cells 42, fluid evaporation and, consequently, reagent loss is minimized. Also, the closed configuration improves temperature control.

In one embodiment, the gasket 46 may be made of a deformable, chemically inert rubber or plastic that retains the liquid applied to the flow chamber. The opening of the gasket may be sized to maximize the field of view of an image acquisition window of an image acquisition unit 34. The inlet and outlet ports 52 and 54 may be disposed away from the image acquisition window. In one embodiment, the inlet and outlet ports may be positioned in the gasket 46 or upon the lid 50. The inlet and outlet ports 52 and 54 may be similarly sized so that the in-flow rate and the out-flow rate are coordinated to achieve a desirable flow rate across the sample.

The solid support-receiving member 44 may be compatible with a range of chemical and temperature variations. In one embodiment, the slide-receiving member 44 may comprise a locking mechanism for securing the slide 48 in the chamber. Non-limiting examples of the locking mechanism may comprise a base and pin or tab system, or a magnet based system.

In some embodiments, the flow cells 42 may be disposed on the sample stage 40. The sample stage 40 may be operatively coupled to a sample processing unit 32 and the image acquisition unit 34. In the illustrated embodiment, the sample stage 40 may be a platform or stage of the image acquisition unit 34 of the system 30.

The sample stage 40 may comprises a continuous or discontinuous platform. The sample stage 40 may comprise one or more discrete portions to dispose one or more groups of the samples. Advantageously, both sample processing and imaging operations may occur on the same stage as the staining operation is very less sensitive to motions of the sample stage 40 occurring due to imaging of the samples in the other group In some embodiments, the sample stage 40 may comprise a driving device 38, such as a mechanical drive member, or an actuator to facilitate the sample stage 40 to move translationally, rotationally, or both. In some embodiments, rotational actuators may be used for rotational movements of the sample stage 40, and translational actuators may be used for translational movements of the sample stage 40.

In one embodiment, the driving device 38 may comprise a mechanical drive member, such as a motor, in operative association with the sample stage 40. In one embodiment, the sample stage 40 may be coupled to a shaft of a mechanical driver member; such as drive motor, thereby enabling the mechanical drive member to rotate the sample stage 40. In one embodiment, the sample stage 40 may be operatively coupled to a stepper motor. The stepper motor is usually compact in size and is an electromagnetic device that converts electric pulses into discrete mechanical motion. The stepper motor employs a stator and a rotor. Fine control of the rotor position may be obtained by increasing number of detent positions on the rotor. The sample stage 40 may either employ an open loop command, close loop command, feedback mode of command, or combinations thereof. The sample stage 40 may employ one or more stepper motors.

The sample processing unit 32 may comprise one or more sub-units to perform various processing steps involved in the processing of a sample. In one embodiment, the sample processing unit 32 may comprise a staining subunit and a destaining or bleaching subunit. The staining subunit may be configured to provide a staining agent for staining one or more of the plurality of samples. The staining subunit may comprise one or more staining agents. The staining subunit may be configured to provide the various agents simultaneously or sequentially. By way of example, the staining subunit may provide different staining agents to one or more of the flow cells 42.

In certain embodiments, having a common sample stage 40 for sample processing and imaging allows the sample to be exposed to a series of reagents without manual intervention thereby eliminating realignment of the sample on the microscope stage for image acquisition or registration. This is particularly useful for multiplexed staining and imaging as images acquired after each staining step may be superimposed to form a composite image.

Accessory devices, such as heating elements or agitation elements (e.g. an acoustic piezoelectric component) may be operatively coupled to the sample stage 40 or the flow cells 42. In one example, the accessory devices may be positioned away from the image capture window through which a microscope, coupled to a camera, may capture images of the sample during the various phases of processing.

The sample stage 40 may be operatively coupled to an illumination source 58. The illumination source 58 may be configured to illuminate at least a portion of the samples disposed on the sample stage 40. Non-limiting examples of the illumination source 58 may comprise a laser source, light emitting diode, white light source, or combinations thereof.

In certain embodiments, the system 30 may comprise a fluidic control device to control fluidic delivery and solution temperature for the flow cells 42. The fluidic control device may be disposed upstream of the flow cells 42. The fluidic control device may comprise reservoirs, flow sensors, mixing chambers, and degassers to prepare one or more reagents prior to injection of reagents in one or more flow cells 42. The fluidic control device may be configured to deliver the reagent and samples to the flow cells 42. In one embodiment, the fluidic control device may be configured to prevent the need to premix and store reagents. For example, the fluidic control device may be configured to prevent the need for premixing and storing reagents that may have limited stability or shelf life. The fluidic control device may be in fluidic communication with the inlet port 52 and outlet port 54 of the flow. In one embodiment, the premixer may be based on a chamber design or a tube design. The chamber design may include a small vessel with inlet and outlet ports and containing a mechanical mixer. In some embodiments, the solutions are mixed at the molecular level by using a premixer to intersperse the reactants immediately prior to the reagent is introduced into the flow cell 42. In one embodiment, mixing times for the reactants may be maintained sufficiently long to generate the reagent and sufficiently limited to prevent decomposition of the reagent. In some embodiments, the system 30 may comprise a temperature control device to control solution temperature for the flow cells 42.

In certain embodiments, the system 30 may comprise the image acquisition unit 34 to acquire signals from the processed samples. In one embodiment, the image acquisition unit 34 may comprise a microscope operatively coupled to an image-receiving device, such as but not limited to, a camera. The image acquisition unit 34 may further comprise optical elements, such as but not limited to, an objective lens. In some embodiments, the image acquisition unit 34 may be configured to record images in more than one field of view on the sample slide to locate and map multiple stained entities in the sample.

In certain embodiments, the image acquisition unit 34 is divided by color channel into two or more separate optical engines. In certain other embodiments, the image acquisition unit 34 is divided by magnification factor into two or more separate optical engines. In other embodiments, the image acquisition unit 34 is divided by acquisition numerical aperture into two or more separate optical engines. In still other embodiments, the image acquisition unit 34 is divided by both color channel and magnification factor into two or more separate optical engines.

In some embodiments, the image acquisition unit 34 may be operatively coupled to an image capture window of the flow cells 42 such that a sample is positioned within a field of view of the image acquisition unit 34. The image capture window may be defined by the substrate (e.g., microscope slide or tissue micro array) upon which the sample is disposed. The image capture window may include an optically transmissive material on the underside of the sample substrate or support. In one example, the image acquisition unit 34 may be disposed adjacent a flow cell 42 that is being imaged. The image acquisition unit 34 may be configured to record images of the sample while the sample is disposed in the flow cell, that is, while the sample is disposed between the slide or sample support and the flow channel housing.

In some embodiments, the image acquisition unit 34 may be in communication with a signal processing unit 56. The signal processing unit 56 may be configured to process data acquired by the image acquisition unit 34. The data acquired by the image acquisition unit 34 may be transmitted to the signal processing unit 56 for processing. In one example, the signal processing unit 56 may form part of the system 30. In another example, the signal processing unit 56 may be a separate entity that may be operatively coupled to the system 30.

In some embodiments, the signal processing unit 56 may be configured to analyze the image acquired by the image acquisition unit 34. In one embodiment, the image acquisition unit 34 may acquire images in real-time. In one example, the signal processing unit 56 may process the images in real-time. In another example, the signal processing unit 56 may store the images such that the images may be accessed, processed, or both at a later time. The signal processing unit 18 may be operatively coupled to a display unit 64 to display the processed data.

In certain embodiments, the signal processing unit 56 may comprise a microprocessor, microcontroller digital signal processor (DSP), field programmable gate array (FPGA), or a combination thereof. The system 10 may also comprise a storage device for at least temporarily storing one or more images or information regarding regions of interest. The storage device may comprise, but is not limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the signal processing unit 56, and yet still be accessed through any suitable connection device or communications network including, but not limited to, local area networks, cable networks, satellite networks, and the internet, regardless whether hard wired or wireless. In one embodiment, the embedded DSP function of FPGA may generate individual images of scattering, and fluorescence at different wavelengths, simultaneously.

The signal processing unit 56 may be operatively coupled to a control unit 60. In some embodiments, the control unit 60 may be in communication with a control input or user interface 62. The user interface 62 may be a touch screen or keyboard, pad or stylus allowing the operator or user to select options by touching displayed graphics, icons, and the like. The control unit 60 may be configured to control at least in part the sample processing unit 32, image acquisition unit 34, movements of sample stage 40, or combinations thereof. For example, the control unit 60 may control one or more components of the sample processing unit 32 such as but not limited to, a premixer, a mixing unit, pumps, valves, or combinations thereof. In one embodiment, one or more components of the image acquisition unit 34, such as but not limited to, a microscope, and a camera may be controlled by the control unit 60.

The control unit 60 may comprise a central processing unit (CPU). The control unit 60 may further comprise one or more memory elements. The control unit 60 may be able to control the movements of the sample stage 40. The control unit 60 may be configured to instruct the driving member 63 of the sample stage 40 to facilitate desirable movements of the sample stage 40. In one embodiment, the control unit 60 may form part of the system 30. In another embodiment, the control unit 60 may be external to the system 30. In one example where the control unit 60 is external to the system 30, a CPU may be operatively coupled to the system 30 (e.g., the sample processing unit 32, or image acquisition unit 34). The control unit 60 may be coupled to the system 30 using a wired or wireless connection. In one embodiment, the control unit 60 may be wireless or hardwired, and may be located at a remote location from system 30.

In certain embodiments, the control unit 60 may control the sample processing and imaging of the samples. In one example, in a closed loop system, the control unit 60 may transmit a signal to the flow cells 42 instructing the flow cells 42 to stop the staining step and to move to the next step, such as the rinsing step. Similarly, for the imaging of the samples, the control unit 60 may estimate an imaging time for a sample. In one embodiment, the time taken for each of the processing steps for the sample processing may be pre-fed to the control unit 60. Further, the time taken for imaging of the samples may also be pre-fed to the control unit 60 to enable the control unit to make a decision as to when to stop a certain step and move to the next step. Data, such as processing time, and imaging time may be pre-fed in the system 30 using the user interface 62. In one example, based on the estimated or pre-fed imaging time of a sample, the control unit 60 may instruct the sample stage 40 to present the next sample to the image acquisition unit 34. In one embodiment, for a given number of samples, the control unit 60 may divide the samples in two or more groups, based on factors, such as but not limited to, an assay type, individual processing time of the samples, individual imaging time of the samples, number of image acquisition units, or combinations thereof.

Figure 3:
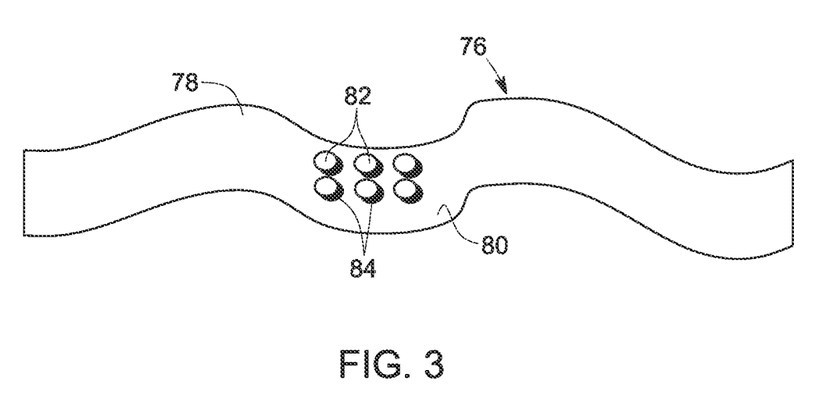
FIG. 3 is a schematic representation of an example sample conveyance unit configured to simultaneously process and sequentially image a plurality of samples, wherein the sample conveyance unit comprises a conveyor belt.

FIG. 3 illustrates an example sample conveyance unit 76. In the illustrated embodiment, the sample conveyance unit 76 comprises a conveyor belt 78. A portion 80 of the conveyor belt 78 comprises a plurality of flow cells 82. The flow cells 82. The flow cells 82 may be arranged as an array or may be disposed in rows, columns or in any other regular or irregular arrangement. Biological samples 84 may be disposed in the flow cells 82 for sample processing and imaging. In some embodiments, the various biological samples 84 may be processed simultaneously using for example, a robotic arm. In these embodiments, some of the steps of the sample processing and imaging may be performed simultaneously, while some other steps may be performed at different times. By way of example, if two samples are to be stained with different stains having different incubation periods, the stains may be mixed with the samples concurrently; however, the steps after the incubation may be performed at different times depending on the incubation period for the respective stains. The samples may be disposed in the flow cells 82 in a continuous or batch process.

The conveyor belt 78 may be configured to transport the samples between the sample processing unit and image acquisition unit. In one example, the conveyor belt 78 may comprise two or more portions 80 to receive the samples.

Figure 4:
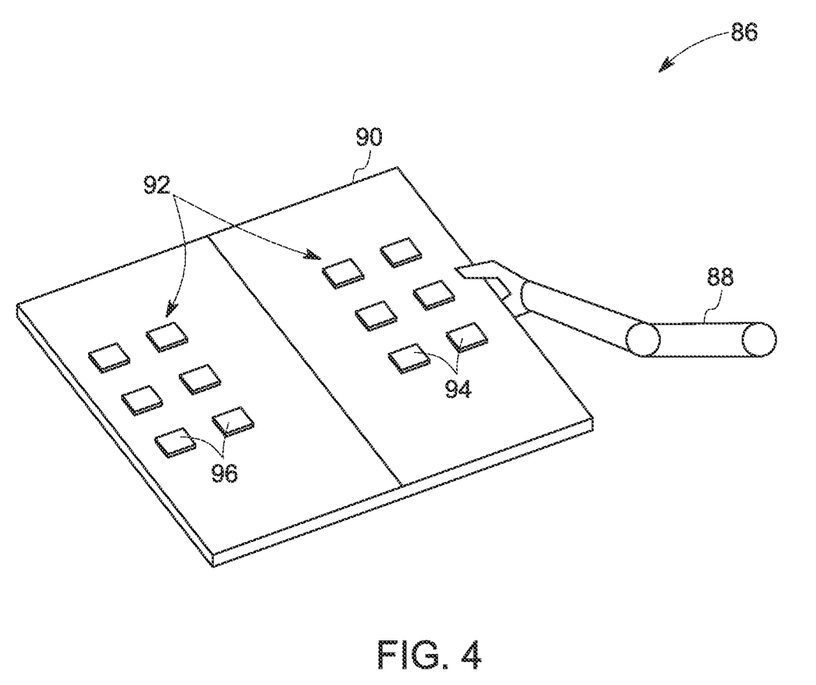
FIG. 4 is a schematic representation of an example sample conveyance unit configured to simultaneously process and sequentially image a plurality of samples, wherein the sample conveyance unit comprises a moveable arm and a sample receiving portion.

FIG. 4 illustrates an example of a surface of a sample conveyance unit 86 comprising a moveable arm 88 and a sample receiving portion 90 for receiving the samples. The sample conveyance unit 86 may be configured to move the samples between a sample processing unit and the image acquisition unit. In one embodiment, the moveable arm 88 may be configured to undergo a translational motion along one or more directions, rotational motion along one or more directions, or both. The moveable arm 88 may comprise a robotic arm. In one embodiment, the moveable arm 88 may be integral to the sample processing unit, or the image acquisition unit. In another embodiment, the moveable arm 88 may be external to the system. In one embodiment, the moveable arm 88 may be configured to receive samples from a sample repository.

The sample receiving portion 90 is configured to receive samples in the flow cells 94. In the illustrated embodiment, the sample receiving portion 90 may comprise two groups 92 of flow cells 94. The groups 92 may each comprise a plurality of flow cells 94. The groups 92 may be disposed in discrete locations of the sample stage 90. The groups 92 may be positioned such that samples 96 disposed in the flow cells 94 of one group may be subjected to staining, while the samples 96 disposed in the flow cells 94 of another group 92 may be subjected to imaging.

The number of flow cells 94 in the two groups 92 may be same or different. The number of flow cells 94 may be determined based on the processing time and imaging time of the samples. In one embodiment, the optimal number of samples disposed in each of the groups 92 may be determined based on the ratio of the imaging time and the sample processing time for an individual sample. By way of example, for two groups having same number of samples, if the step of sample processing for a single sample requires 60 minutes, and the imaging time is 10 minutes for each sample. The time required for the simultaneous processing of the samples may be 60 minutes. Hence, for optimal usage of the sample processing and imaging units, each group may comprise 6 samples in this non-limiting example.

Figure 5:
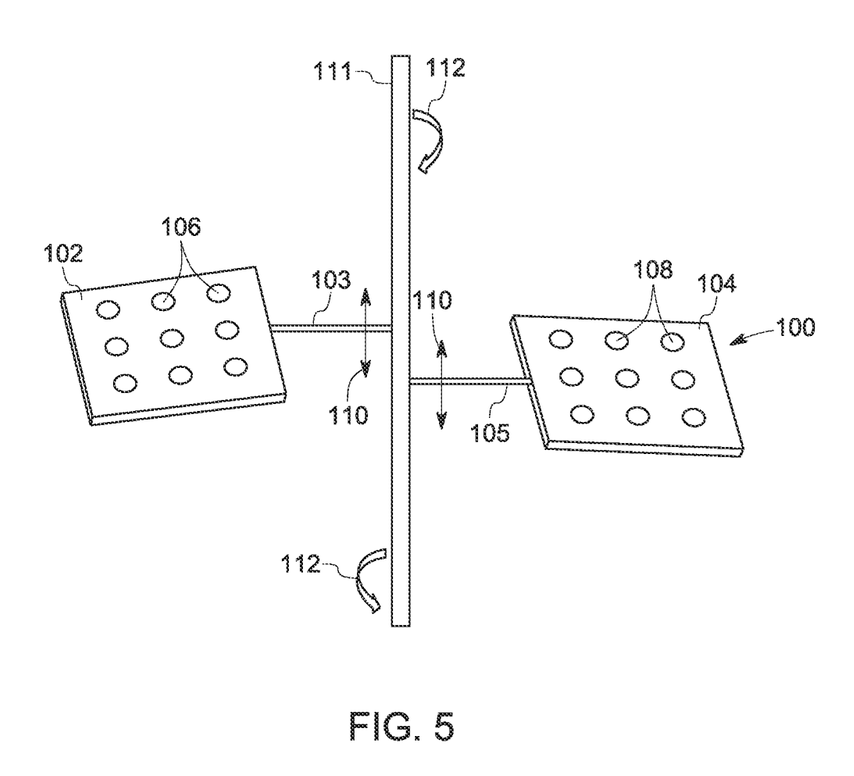
FIG. 5 is a schematic representation of an example sample stage comprising two discontinuous portions.

In certain embodiments, two or more portions of the sample stage may be disposed on the same horizontal plane. In another embodiment, the groups may be disposed on different horizontal planes. FIG. 5 illustrates an example of a sample conveyance unit 100 comprising two discrete portions 102 and 104. The portion 102 of the sample stage having a group of flow cells 106 may be disposed in one horizontal plane, and other portion 104 of the sample stage 100 having another group of flow cells 108 may be disposed in another horizontal plane. The two portions 102 and 104 of the sample stage 100 may be vertically aligned or staggered. The portions 102 and 104 may be coupled to a common shaft 111 using arms 103 and 105, respectively. In one embodiment, the arms 103 and 105 may be extendable to facilitate transporting the flow cells 106 and 108 to the sample processing unit and image acquisition unit.

In one example, the discrete portions of the sample stage 100 may be aligned in vertical plane to satisfy space requirements in the horizontal plane. The portions 102 and 104 may be configured to undergo translational movements, rotational movements, or both to be selectively operatively coupled to the sample processing unit or image acquisition unit or both. The arrows 110 represent translational movements of the sample stage 100, arrows 112 represent rotational movements of the portions 102 and 104 of the sample stage 100. The portions 102 and 104 of the sample stage 100 may be configured to move vertically to be operatively coupled to the sample processing unit or the image acquisition unit as required.

Advantageously, methods and systems increase the throughput for processing and imaging of the plurality of samples. In some embodiments, the throughput of the system may be increased while reducing factors contributing to errors in the process and disturbances in the samples. In certain embodiments, a throughput of the processing and imaging system may be enhanced by maximizing the usage of the image acquisition unit, such as but not limited to a microscope. Typically, samples are processed away from the imaging unit in an off line location, and the processed samples are transferred manually from the off line location to the imaging stage. In one embodiment, the system may be configured to process the samples such that it may not be required to transfer the processed samples from an off line location to the sample conveyance unit for imaging. In certain embodiments, the methods may reduce a cycle time for a plurality of samples for a given set of stains antibodies, thereby improving the throughput.

In certain embodiments, sample processing may comprise a series of steps, such as, but not limited to, rinsing the sample, binding of reagents to the specific parts of the sample, activation of the reagents. Further, each treatment step may comprise a plurality of individual treatment steps. In certain embodiments, the sample processing for a sample may generally comprise positioning a biological sample, such as a tissue section, on a microscope slide or well, in a flow cell, applying a fluorescent label or a lumiphore to the sample in a manner to allow sufficient contact time between the lumiphore and the sample which are typically in the range of 30 to 60 minutes depending on the concentration and type of label used, and rinsing the biological sample by applying a wash solution, for example an appropriate buffer solution to wash away any unbound fluorescent label or lumiphore. In some embodiments, the sample processing may further comprise preparing the slide prior to disposing the same on the slide, disposing a medium, bleaching the sample to at least partially remove the stain, and to prepare the sample for next staining cycle. Each of the staining, rinsing and bleaching steps may be accomplished by flowing a solution containing a particular reagent over the biological sample positioned within the flow cell. Alternatively, the solutions may be dispensed onto sample and optionally a cover may be applied to help spread the solutions and maximize coverage on the sample.

Subsequent to the processing, the processed samples may be transported to the imaging unit for imaging. Imaging may be performed at two or more stages during the sample processing, also referred to as staining cycle. In one embodiment, each staining cycle may comprise staining at least a portion of the biological sample, rinsing away at least a portion of the stain to reduce background fluorescence, bleaching away the stain. The staining cycle may be repeated for multiple stains. The step of imaging may be performed after one or more of staining, rinsing and bleaching. Alternatively, imaging may be performed after each of staining, rinsing and bleaching. In one embodiment, the imaging may be performed at time intervals that are greater than exposure time of the sample.

The step of imaging the samples may comprise acquiring a signal from the image of the processed sample. Wherein, acquiring the signal comprises acquiring the signal through an image acquisition window.

In certain embodiments, the method comprises real-time monitoring of at least a portion of the tissue along with a real-time determination of whether the desired state has been reached (e.g., an extent to which bleaching, staining or rinsing has occurred).

Figure 6:
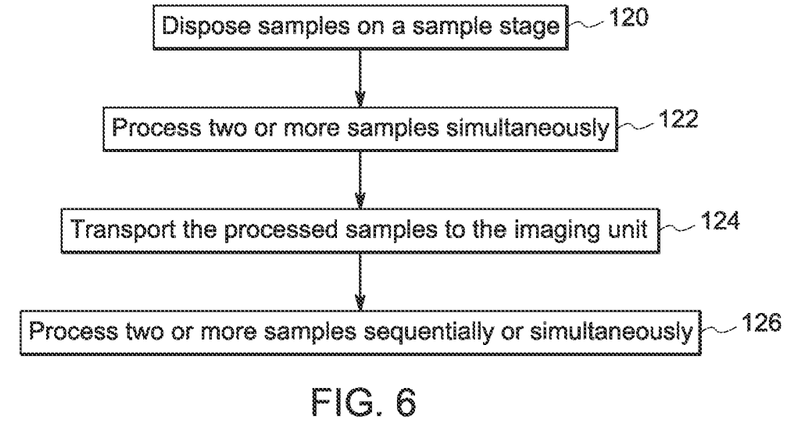
FIG. 6 is a flow chart of an example method for simultaneous processing and sequential imaging of samples.

FIG. 6 illustrates a flow chart representing an example sequence of events for high throughput sample processing and imaging of a plurality of samples. At step 120, the samples may be disposed on a sample stage. The samples may be disposed in corresponding flow cells disposed in a sample conveyance unit. The sample conveyance unit may be operatively coupled to a sample processing unit and an image acquisition unit. At step 122, two or more of the plurality of samples may be processed simultaneously. In one example, a plurality of samples may be processed, for example, a plurality of samples may be stained simultaneously. At step 124, at least the processed samples may be transported to the imaging unit. The processed samples may be transported by moving the sample stage in a translational movement, rotational movement, or both. At step 126, the processed samples may be imaged in a sequential manner using an imaging unit. In some embodiments, the system may be configured to process at least one sample from the plurality of samples while imaging another sample from the plurality of samples.

In certain embodiments, the methods may be used for multiplexed applications. In one embodiment, after imaging, the samples may be processed again, for example, the samples may be stained using another stain that does not interact with the earlier present stain. Alternatively, the samples may be bleached to remove the first stain. Subsequently, the samples may be stained using another stain. In one embodiment, the samples may be imaged after bleaching and prior to being stained with another stain.

Assuming that sample processing time includes both bleaching and staining times for the samples. Further, assuming that the imaging of the samples is performed after staining, and not after bleaching, Eq. (1) represents time taken for processing and imaging a plurality of samples having n number of samples. Eq. (1) is reproduced below:

$$\text{Time for one round} = [t_s + nt_i] \qquad \text{Eq. (1)}$$

where, n is number of samples or flow cells, $t_s$ is stain time for a sample, $t_i$ is imaging time for a sample.

Eq. (2) represents processing rate per sample.

$$\text{Processing rate per sample} = 1/[t_s/n + t_i] \qquad \text{Eq. (2)}$$

In some embodiments, the approach of FIG. 5 may be used when a cumulative imaging time of the samples is relatively greater compared to a processing time of a sample.

Figure 7:
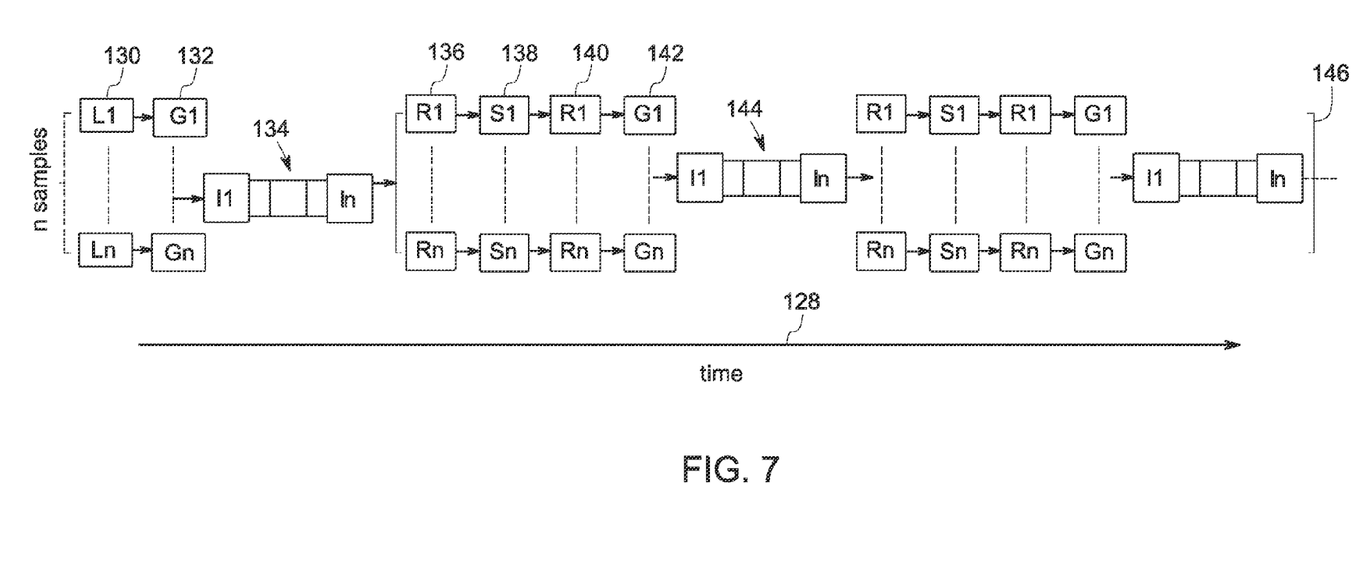
FIG. 7 is a detailed flow chart of an example method for simultaneous processing and sequential imaging of samples.

FIG. 7 illustrates an example detailed flow chart comprising individual processing and imaging steps. The samples may be disposed on a sample stage. The sample stage may be operatively coupled to a sample processing unit and an imaging unit. In the illustrated embodiment, samples may be processed simultaneously. That is, the samples may be processed during the same time period. Time is generally represented on abscissa 128 to indicate simultaneous or sequential order of events. For example, the samples may be simultaneously disposed in the flow cells as represented by the reference numeral 130. A medium may be disposed simultaneously in the flow cells as represented by the reference numeral 132. The samples may be imaged (134). The samples in the flow cells may be imaged sequentially. Hence, the total imaging time is a sum of the individual imaging times of the samples. Following imaging, the samples may be processed. For example, the samples may be rinsed (136), stained (138), rinsed post staining (140), and disposed in a medium (142). The various processing steps may be performed simultaneously for the various samples, thus greatly reducing the total processing time for the samples. Further, the samples may be processed while still being disposed on the sample stage. In some embodiments, the sample processing unit and sample stage are configured to facilitate processing of the sample while being disposed on the sample stage. Hence, the samples are not required to be transferred between a sample processing location and an imaging location. Accordingly, samples of a group may be made available for imaging as soon as the imaging unit is done imaging samples of another group. The samples may be imaged sequentially (144). The processing and imaging steps may be repeated as desirable as represented by reference numeral 146.

Figure 8:
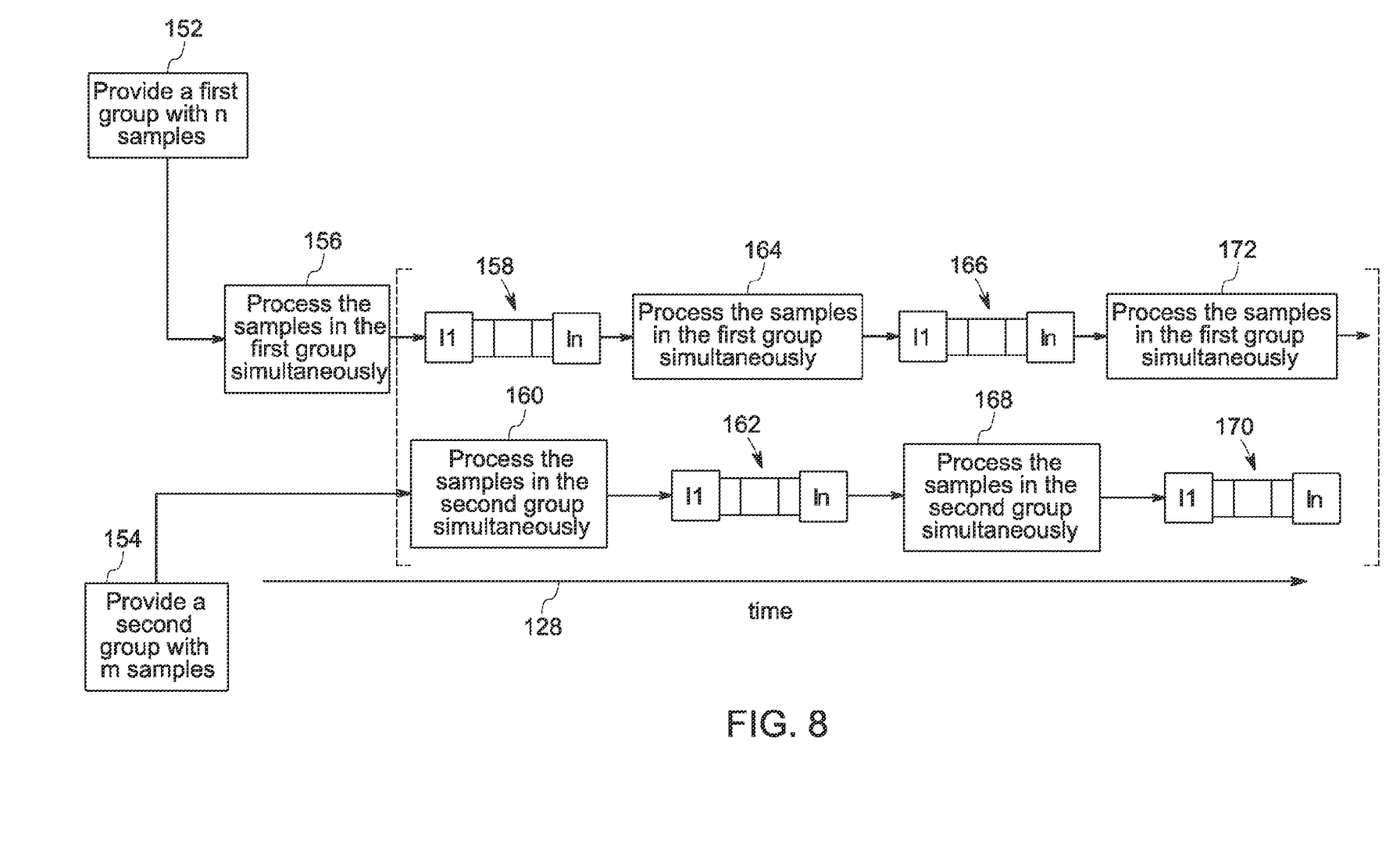
FIG. 8 is a flow chart of an example method for processing and imaging two or more groups of samples.

FIG. 8 illustrates a block diagram for an example sequence of events with respect to time. In the illustrated embodiment, processing and imaging of groups of samples is planned to maximize the throughput of the system while reducing idle times for sample processing and/or imaging units.

In the illustrated embodiment, two groups of flow cells, generally represented by reference numerals 152 and 154 may be provided. The flow cells may be disposed on a sample stage. The first group 152 may comprise n number of samples, and the second group may comprise m number of samples. The number of samples in the two groups may depend upon individual processing and imaging time required for the samples in the two groups. By way of example, if a sum of the processing time and imaging time for the samples in the first group 152 is relatively lower than a sum of the processing time and imaging time for the samples in the second group 154, then the number of samples in the first group may be more than the number of samples in the second group (n>m). Similarly, if a sum of the processing time and imaging time for the samples in the two groups 152 and 154 is substantially similar, then the number of samples in the two groups may be the same (n=m). As illustrated by block 156, the samples of the first group 152 may be processed, for example, stained and rinsed. The samples may be processed simultaneously. The processed samples may then be imaged in a sequential manner (158).

While the samples of the first group 152 are being imaged (158, 164, 162), samples of the second group 154 may be processed (160, 156). Imaging the samples of the first group while the samples of the second group are being processed may be represented by overlapping time ranges for imaging of the samples of the first group 152 and processing of the samples of the second group. Similarly, while the samples of the second group 154 are being imaged (132, 170), the samples of the first group may be processed (164, 162). However, it should be noted that in some instances the processing time of the samples of one group may be smaller than a cumulative imaging time of the samples of the other group. In these instances, the samples of the second group may be available for imaging while the samples of the first group are still being imaged.

In certain embodiments, a minimal idle time for the sample processing unit may be achieved when the blocks (156, 160, 164, 156 and 162) that represent the sample processing of first group 152 or second group 154 may collectively occupy the abscissa with minimal time differences between any two consecutive processing blocks. Hence, the planning may be done accordingly. Similarly, minimum idle time for the image acquisition unit may be achieved when the imaging blocks (158, 132, 166 and 170) are disposed adjacent each other on the time axis with minimal or no gap between two consecutive imaging blocks. Thus, the method of FIG. 7 may attain maximum utilization of imaging and processing units by selecting appropriate group size of the samples.

In one embodiment, assuming that the sample processing time comprises both bleaching and staining times, and imaging is performed only after staining (and not after bleaching) Eq. (3) represents time taken for processing and imaging n number of samples. Eq. (3) is represented below:

$$\text{Time for processing and imaging a group of samples having } n \text{ samples} = [t_s + nt_i] \quad \text{Eq. (3)}$$

where, n is number of flow cells or samples in one group, $t_s$ is processing time for a sample stain time for a sample, $t_i$ is imaging time for a sample, and $n_{total}$ is total number of samples on the sample stage. The total number of samples is represented below in Eq. (4).

$$n_{total}/2 = t_s/t_i \quad \text{Eq. (4)}$$

Figure 9:
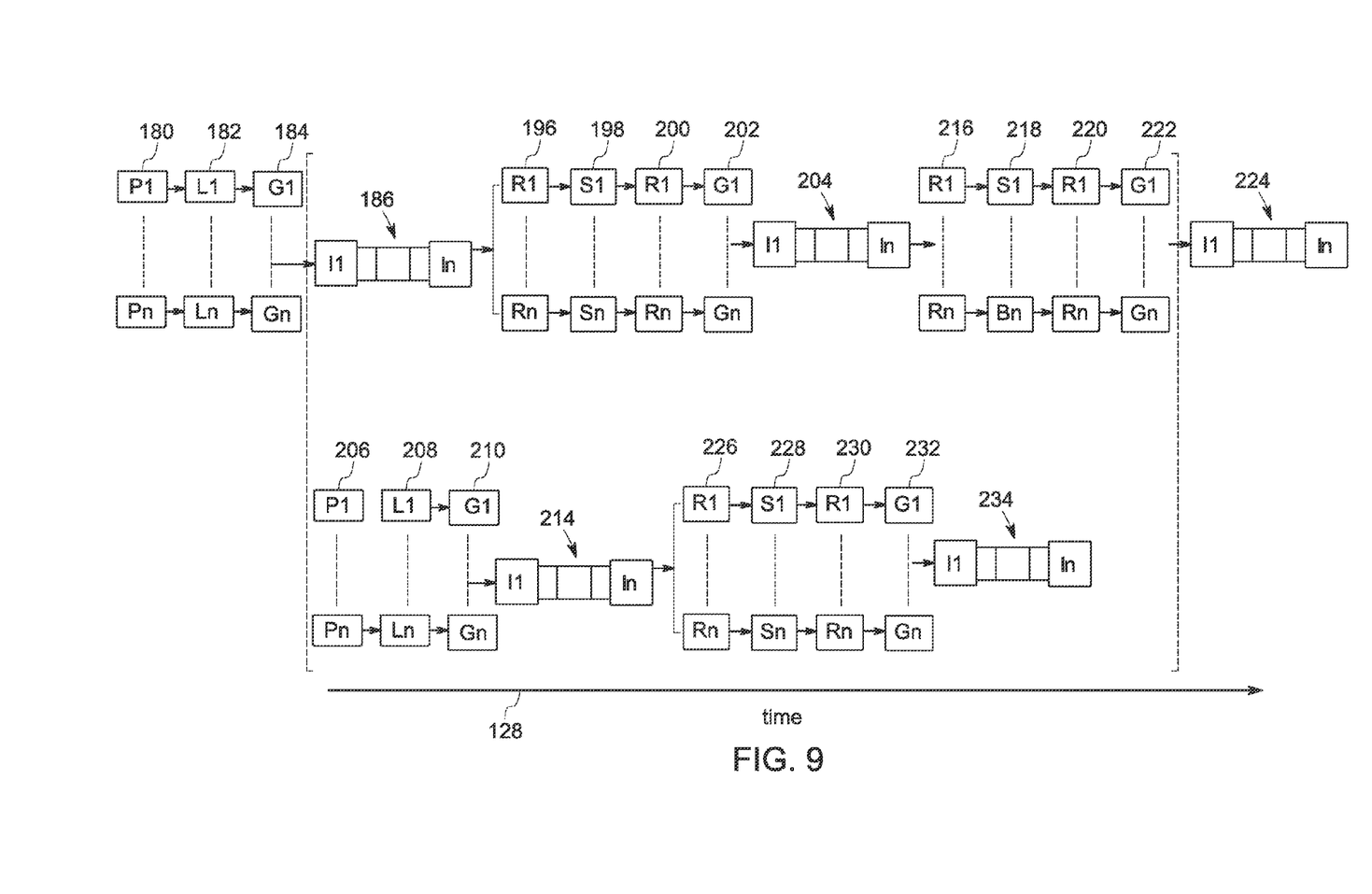
FIG. 9 is a detailed flow chart of an example method for processing and imaging two or more groups of samples.

FIG. 9 illustrates a specific example for processing two groups of samples. In the illustrated embodiment, a first group comprising n samples and a second group comprising m samples may be provided. Samples of the first group may be processed simultaneously. For example, the steps of applying a primer layer (180) on slides, disposing the samples on the slides (182), and disposing a medium on the samples (184) may be performed simultaneously for the n number of samples of the first group. Next, the processed samples may be presented to the imaging unit for imaging (186). While the samples of the first group are being imaged by the imaging unit, the samples of the second group may be provided to the sample processing unit for processing. The samples may be transported to the imaging unit and the sample processing unit using a sample conveyance unit. In the illustrated embodiment, the processing of the samples of the second group may comprise applying a primer layer (206) on the slides, disposing the samples on the slides (208), and disposing a medium on the samples (210). Next, the processed samples may be presented at the imaging unit for imaging (214). While the samples of the second group are being imaged, the samples of the first group may be presented to the sample processing unit for further processing. In one embodiment where the two groups of samples are disposed in discrete locations on a surface of the sample stage, the samples may be provided to the imaging unit and sample processing unit by rotating the sample stage by a determined angle depending on the position of the imaging and sample processing units relative to the sample stage.

As illustrated, the samples may be rinsed (196), stained (198), rinsed after staining (200) and disposed in a medium (202). Next, the processed samples of the first group may be presented to the imaging unit for imaging (204). While the processed samples of the first group are being imaged, the samples of the second group may be presented to the sample processing unit for further processing. In one embodiment, the processing may comprise rinsing (226), staining (228), rinsing after staining (230) and disposing in a medium (232). Next, the processing samples of the second group may be imaged (234). While the samples of the second group are being imaged, the sample of the first group may be further processed. The processing may comprise rinsing (216), bleaching (218), rinsing after bleaching (220), and disposing in a medium (222). The processed samples may be presented to the imaging unit for imaging (224). At the same time, the samples of the second group may be presented to the sample processing unit for further processing comprising rinsing (216), bleaching (218), rinsing after bleaching (220), and disposing in a medium (222). The process may be repeated for more number of stains.

Hence, the samples of the first and second groups may be processed and imaged in a time efficient manner with least operator intervention while minimizing the idle times of the sample processing and imaging units of the system.

It should be noted that three or more groups of flow cells may also be processed and imaged using a similar approach.

The systems and methods disclosed herein may find applications in various fields, such as but not limited to analytic, diagnostic, and therapeutic applications in biology and medicine. In some embodiments, the systems and methods disclosed herein may find applications in histochemistry, particularly, immunohistochemistry. Analysis of cell or samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A system for processing and imaging a plurality of samples, comprising:
    a sample processing unit configured to process one or more of the plurality of samples;
    an image acquisition unit operatively coupled to the sample processing unit; and
    a sample conveyance unit configured to transport one or more of the plurality of samples to the sample processing unit, image acquisition unit, or both,
    wherein the system is configured to process at least one sample from the plurality of samples while simultaneously imaging another sample from the plurality of samples.

2. The system of claim 1, wherein the sample conveyance unit comprises:
    a sample stage configured to receive the plurality of samples; and
    a driving member configured to provide a translational movement, rotational movement, or both to the sample stage.

3. The system of claim 2, wherein the sample stage comprises a continuous surface.

4. The system of claim 1, wherein the image acquisition unit comprises one or more microscopes.

5. The system of claim 4, wherein the sample conveyance unit is an integral part of the one or more microscopes.

6. The system of claim 1, wherein the image acquisition unit is divided by color channel into two or more separate optical engines.

7. The system of claim 1, wherein the image acquisition unit is divided by magnification factor into two or more separate optical engines.

8. The system of claim 1, wherein the image acquisition unit is divided by acquisition numerical aperture in to two or more separate optical engine.

9. The system of claim 1, wherein the image acquisition unit is divided by both color channel and magnification factor into two or more separate optical engines.

10. The system of claim 9, wherein a sample is grouped into said first and second plurality of samples based on a scan area of each sample, as well as information about an assay, to achieve minimum time-to-completion grouping of samples.

11. An automated method for processing and imaging a first and second plurality of samples, comprising:
    processing at least one sample from the first plurality of samples;
    imaging the at least one sample from the first plurality of samples, while also being capable of simultaneously processing at least one sample from the second plurality of samples; and
    imaging the at least one processed sample from the second plurality of samples,
    wherein providing the first and second plurality of samples comprises disposing the first and second plurality of samples in two discrete locations on a sample stage.

12. The method of claim 11, further comprising acquiring a low magnification image of each sample that relates scan area of each sample and grouping the samples into the first and second plurality of samples based on at least the scan area of each sample.

13. The method of claim 11, further comprising imaging the first and second plurality of samples before any processing is performed to obtain background Images.

14. The method of claim 11, further comprising imaging one of the first or the second plurality of samples, prior to processing, while the other set of sample is being processed, to establish background images.

15. An automated method for processing and imaging a first and second plurality of samples, comprising:
    processing at least one sample from the first plurality of samples;
    imaging the at least one sample from the first plurality of samples, while also being capable of simultaneously processing at least one sample from the second plurality of samples; and
    imaging the at least one processed sample from the second plurality of samples,
    wherein providing the first and second plurality of samples comprises disposing the first and second plurality of samples on a sample stage.

16. The method of claim 15, wherein the sample stage is a stage of an imaging device.

* * * * *